United States Patent [19]

Sandman et al.

[11] Patent Number: 4,613,468

[45] Date of Patent: Sep. 23, 1986

[54] METHOD FOR PREPARING AROMATIC AND OLEFINIC ORGANOSELENIUM AND ORGANOTELLURIUM COMPOUNDS

[75] Inventors: Daniel J. Sandman, Acton; James C. Stark, Quincy; Lewis A. Acampora, Cambridge, all of Mass.

[73] Assignee: GTE Laboratories Incorporated, Waltham, Mass.

[21] Appl. No.: 570,169

[22] Filed: Jan. 12, 1984

[51] Int. Cl.⁴ .................. C07C 163/00; C07C 165/00
[52] U.S. Cl. ...................... 260/550; 540/1; 423/509; 528/397
[58] Field of Search ............ 260/550, 239 R; 528/397; 423/509

[56] References Cited

U.S. PATENT DOCUMENTS 3,965,049  6/1976  Grushkin et al. ............ 260/239 R

OTHER PUBLICATIONS

D. Sandman et al., J. Chem. Soc., Chem. Commun., (1982), 1133-1134.
K. Balodis et al., translation from Zhurnal Organ. Khimii, vol. 15, No. 2, 391-393 (1979).
D. Seyferth et al., J. Am. Chem. Soc., 1981, 103, 5103-7.
Gladysz et al., J. Org. Chem. 43, 1204 (1978).
Gladysz et al., J. Chem. Soc. Chem. Commun., p. 838 (1979).
Clive et al., J. Org. Chem. 47, 1641 (1982).
Bender, S. L. et al., Tetrahedron Letters 23, 1531 (1982).
Battistoni, P. et al., Gazz. Chim. Ital. 111, 5050 (1981).

Primary Examiner—Donald G. Daus
Assistant Examiner—Mary E. Ceperey
Attorney, Agent, or Firm—Hamilton, Brook, Smith & Reynolds

[57] ABSTRACT

This invention constitutes a method of preparing molecular and supramolecular aromatic organic telluride, ditelluride, diselenide and selenide compounds from aromatic halogen compounds which are unactivated toward nucleophilic substitution. The method involves the reaction of an aromatic halide with an alkali metal telluride, ditelluride, selenide or diselenide reagent formed from chalcogen and alkali metal trialkylborohydride to yield the corresponding molecular or polymeric aromatic telluride, ditelluride, selenide or diselenide. Further, the alkali metal chalcogenide reagent prepared from alkali metal trialkylborohydrides may also be used to synthesize molecular and polymeric olefinic tellurides and selenides from olefinic halides unactivated toward nucleophilic substitution.

22 Claims, No Drawings

METHOD FOR PREPARING AROMATIC AND OLEFINIC ORGANOSELENIUM AND ORGANOTELLURIUM COMPOUNDS

TECHNICAL FIELD

This invention is in the field of organic chemistry and pertains to methods of preparing aromatic and olefinic organoselenium and organotellurium compounds using alkali chalcogenide reagents prepared from trialkylborohydrides.

BACKGROUND ART

A large number of organoselenium and organotellurium compounds are known in the literature. For comprehensive reviews of organic selenium and tellurium chemistry, see *Organic Selenium Compounds: Their Chemistry and Biology*, D. L. Klayman and W. H. H. Gunther, Ed., Wiley, New York, 1973, and K. J. Ingolic, *The Organic Chemistry of Tellurium*, Gordon and Breach, New York, 1974. Methods of preparing organic tellurides and selenides have involved the formation of alkali metal chalcogen reagents in liquid ammonia. See e.g. Grushkin et al., U.S. Pat. No. 3,965,049. A direct two-step process for synthesis of aromatic molecular and supramolecular organic tellurides, ditellurides and selenides has been described in which an alkali metal chalcogenide reagent is generated without the use of liquid ammonia. Sandman et al., U.S. patent applications Ser. No. 506,690 and Ser. No. 507,156.

The first step is preparation of an alkali metal chalcogenide reagent in an aprotic solvent directly from elemental chalcogen and an alkali metal. An alkali metal is reacted with elemental selenium or tellurium in dipolar aprotic solvents such as dimethylformamide (DMF), N-methylpyrrolidinone (NMP) and hexamethylphosphoramide (HMPA) in 1:1 or 2:1 ratios to give alkali metal chalcogenide reagents $M_2Ch_2$ and $M_2Ch$ (wherein M=Na, K, Li and Ch=Se, Te). The second step involves direct thermal reaction of an aromatic halide with the alkali chalcogenide reagent formed in the first step. The facility of these reactions is noteworthy because nucleophilic substitution in aromatic halides usually requires either strenuous conditions or aromatic substrates activated by electron attracting substituents.

Alkali chalcogenide reagents prepared as described above have proven useful for direct synthesis of both new and previous reported molecular and polymeric ditellurides, tellurides and selenides. See Sandman et al., U.S. patent applications Ser. No. 506,690 and Ser. No. 507,156.

Alkali chalcogenide reagents may also be prepared by reacting a chalcogen with an alkali metal trialkylborohydride in tetrahydrofuran. See Gladysz, J. A. et al. *J. Org. Chem.* 43, 1204–1208 (1978). Alkali metal chalcogenide reagents prepared in this manner have been reacted with alkyl and acyl halides and transition metal systems. For example, Gladysz and coworkers formed alkali metal selenide and diselenide reagents from selenium and lithium trialkylborohydride and synthesized molecular dialkyl selenides and diselenides therefrom. Bender et al. describe a reaction of chloromethyltellurolalkynes with dilithium telluride reagent prepared from tellurium and lithium triethylborohydride to form 1,3-ditelluroles. Tetrahedron Lett. 23, 1531 (1982).

A lithium diselenide reagent formed from selenium and lithium triethylborohydride has been used to synthesize bis-aryl diselenides. Battistoni, P. et al. *Gazz. Chim. Ital.* 111, 505 (1981). However, the aryl halide reactants were O-chloronitrobenzenes, aromatic compounds which have a strong electron withdrawing ring substituent in addition to the halogen atom, namely the nitro ($-NO_2$) group. This strong electron withdrawing group activates the compound toward nucleophilic substitution.

DISCLOSURE OF THE INVENTION

This invention constitutes a method of preparing molecular and supramolecular aromatic organic telluride, ditelluride, diselenide and selenide compounds from aromatic halogen compounds which are unactivated toward nucleophilic substitution, that is, aromatic halogen compounds which do not have strong electron withdrawing groups on the halogen bearing ring or on any ring adjacent to the halogen bearing ring.

The method involves the reaction of an aromatic halide with an alkali metal telluride, ditelluride, selenide or diselenide reagent formed from chalcogen and alkali metal trialkylborohydride to yield the corresponding molecular or polymeric aromatic telluride, ditelluride, selenide or diselenide. The alkali metal chalcogenide reagent is formed from the reaction of elemental tellurium or selenium and an alkali metal trialkylborohydride in an solvent such as an ether. The reagent may be used to prepare aromatic organic compounds having tellurium or selenium containing rings, bis-aryl tellurides and selenides, and polymeric aromatic tellurides and selenides.

Further, the alkali metal chalcogenide reagent prepared from alkali metal trialkylborohydrides may also be used to synthesize molecular and polymeric olefinic tellurides and selenides from olefinic halides unactivated toward nucleophilic substitution, that is, olefinic compounds which have no strong electron-attracting groups (other than halogen) attached to the alkene carbon atoms.

BEST MODE FOR CARRYING OUT THE INVENTION

According to the method of this invention, elemental tellurium or selenium is reacted with an alkali metal trialkyborohydride in solvent to form an alkali metal telluride, ditelluride, selenide or diselenide reagent. These alkali metal chalcogenide reagents cause nucleophilic displacement of halogen substituents in aromatic halides which are not activated in the usual sense for nucleophilic substitution to yield molecular and polymeric aromatic tellurides, ditellurides, selenides and diselenides.

The preparation of some molecular and polymeric aromatic chalcogenides according to the method of this invention is depicted in the chemical equations set forth below. In the exemplary equations, lithium triethylborohydride is the representative trialkylborohydride. As noted below, other trialkylborohydrides may be substituted.

Generally, bis-aryl tellurides and bis-aryl selenides are prepared according to the following equations:

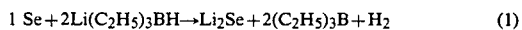

$$1\ Se + 2Li(C_2H_5)_3BH \rightarrow Li_2Se + 2(C_2H_5)_3B + H_2 \qquad (1)$$

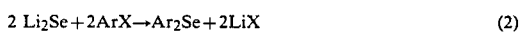

$$2\ Li_2Se + 2ArX \rightarrow Ar_2Se + 2LiX \qquad (2)$$

$$3\ Te + 2Li(C_2H_5)_3BH \rightarrow Li_2Te + 2(C_2H_5)B + H_2 \qquad (3)$$

$$4\ Li_2Te + 2ArX \rightarrow Ar_2Te + 2LiX \qquad (4)$$

wherein Ar is an aromatic hydrocarbon and X is a halogen. Generally, bis-aryl ditellurides and diselenides are prepared according to the following equations:

$$5\ 2Te + 2Li(C_2H_5)_3BH \rightarrow Li_2Te_2 + 2(C_2H_5)_3B + H_2 \qquad (5)$$

$$6\ Li_2Te_2 + 2ArX \rightarrow Ar_2Te_2 + 2LiX \qquad (6)$$

$$7\ 2Se + 2Li(C_2H_5)_3BH \rightarrow Li_2Se_2 + 2(C_2H_5)_3B + H_2 \qquad (7)$$

$$Li_2Se_2 + 2ArX \rightarrow Ar_2Se_2 + 2LiX \qquad (8)$$

wherein Ar is an aromatic hydrocarbon an X is a halogen.

Representative examples of specific bis-aryl chalcogenides which may be formed by the method of the invention are illustrated below. The alkali metal chalcogenide reagents in the equations are formed according to equations (1), (3), (5) and (7).

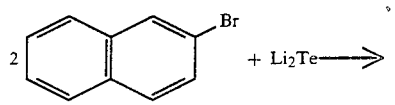

(9)

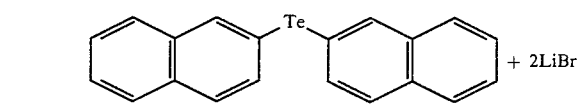

(10)

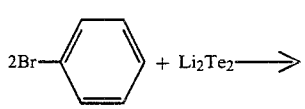

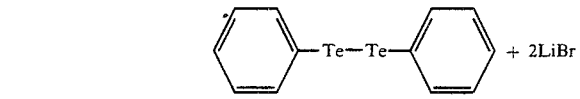

(11)

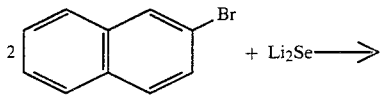

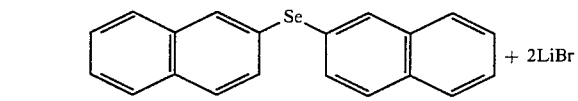

(12)

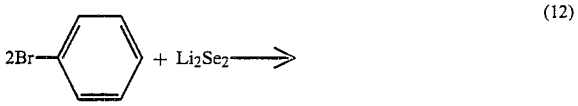

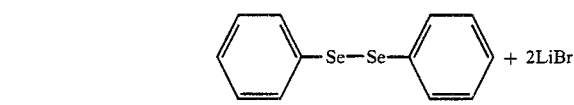

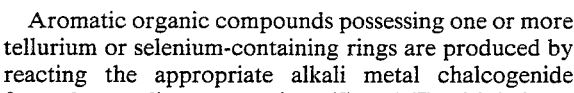

Aromatic organic compounds possessing one or more tellurium or selenium-containing rings are produced by reacting the appropriate alkali metal chalcogenide formed according to equations (5) and (7) with halogenated aromatic compounds having halogen atoms on alternate carbon atoms of two adjacent fused rings. The following equation exemplifies these syntheses.

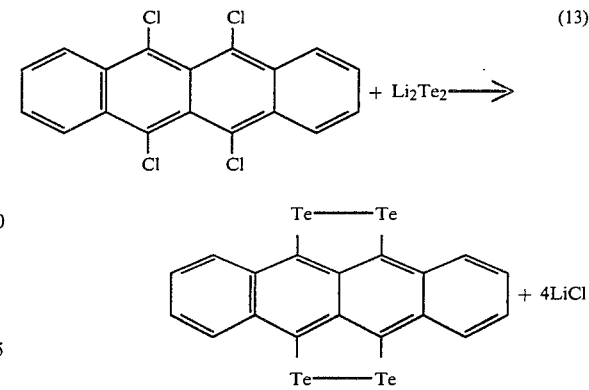

Polymeric aromatic tellurides and selenides are formed according to the following equations.

$$Se + 2Li(C_2H_5)_3BH \rightarrow Li_2Se + 2(C_2H_5)_3B + H_2$$

$$14\ nLi_2Se + nXArX \rightarrow (Ar\text{-}Se)_n + 2nLiX \qquad (14)$$

$$Te + 2Li(C_2H_5)_3BH \rightarrow Li_2Te + 2(C_2H_5)_3B + H_2$$

$$15\ nLi_2Te + nXArX \rightarrow (Ar\text{-}Te)_n + 2nLiX$$

wherein Ar is an aryl hydrocarbon, X is a halogen and n is an integer greater than 2.

Representative examples of polymeric aromatic selenides and tellurides are poly-p-phenylene selenide and poly-p-phenylene telluride as shown in the following equations:

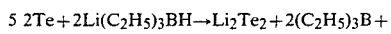

(16)

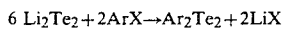

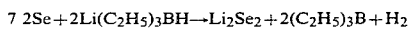

(17)

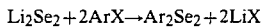

wherein n is an integer greater than 2.

As shown in the equations (2), (4), (6) (10) and (11), alkali metal chalcogenide reagent reacts with aromatic monohalides and aromatic dihalides to give bis-aryl chalcogenides and polymeric aromatic chalcogenides. As used herein, the term "aromatic halide" means a compound having halogen atoms directly attached to a carbon atom of an aromatic hydrocarbon. Examples of the parent aromatic hydrocarbon are benzene, naphthalene, anthracene, tetracene, phenanthrene and biphenyl. To prepare the bis-aryl chalcogenides, a monohaloaromatic component is reacted with the alkali metal chalcogenide reagent. A dihaloaromatic compound is used to prepare the polymeric aromatic chalcogenides. Importantly, the alkali metal chalcogenide reagent reacts the aromatic halide which are not activated toward nucleophilic substitution. These reactants contain only one type of strong electron withdrawing group -the halogen- on the halogenated ring or on a ring adjacent to the halogenated ring. No additional electron withdrawing groups such as nitroso, nitro or oxo substituents are present.

In another embodiment of the method of the present invention, aromatic organic compounds possessing one or more tellurium-containing or selenium-containing rings are produced by reacting alkali metal ditellurium or diselenide reagent with peri-dihalide aromatic substrate (aromatic compound which has halogen atoms substituted on alternate carbon atoms of two adjacent fused rings). The reaction results in the replacement of the two halogen atoms by two linked tellurium atoms resulting in a product having at least one five-membered metallocyclic ring containing linked tellurium or selenium atoms.

The alkali metal chalcogenide reagents also cause the nucleophilic displacement of halogen substituents of olefinic halides to yield molecular and polymeric olefinic telluride and selenides. As used herein, the term "olefinic halide" means a compound having halogen atom(s) attached to a carbon atom in an unsaturated alkene such as the non-conjugated or conjugated monomers, ethylene, propylene, butadiene and the like. The alkali metal chalcogenide reagent formed as in equations (1), (3) or (5) is reacted with a monohalo-olefinic compound to yield bis-olefinic compounds of the general formula

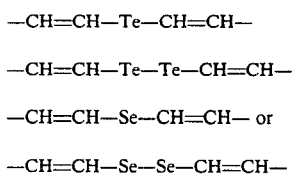

wherein the unsatisfied valences are understood to attach to other hydrocarbon groups. Reaction of the reagent with dihalo-olefinic compounds, i.e., those having a halogen substituent on each of the alkene carbons, yields polymeric compounds having carbon-carbon double bonds and chalcogens. For example, polymers may be formed of the general formulae $+(R_1CH=CH-R_2-Te)_n$ and $+(R_1CH=CHR_2)_n-Se_n$ wherein $R_1$ and $R_2$ are H or a hydrocarbon group and n is an integer greater than 2.

The method of this invention is a two-step process. The first step is the formation of the alkali metal dichalcogenide reagent and the second, reaction of the intermediate reagent with the appropriate aromatic or olefinic halide reactant to produce the desired organoselenium or organotellurium product.

The alkali metal chalcogenide reagents are formed by reacting elemental tellurium or selenium with an alkali metal trialkylborohydride in an ether solvent. The trialkylborohydride in solution is added to a suspension of tellurium or selenium in the same solvent. Usually, the suspension is formed of finely divided chalcogen. Preferably the solvents are ethers such as ethyl ether, tetrahydrofuran or glymes (polyethers). The reaction proceeds readily in ether solvents. Further ethers are convenient because trialkyborohydride reagents are commercially available in ether solvents. The trialkylborohydride may be potassium tri-sec-butyl-borohydride (commercially available in a 0.5 molar THF solution under the trade name K-Selectride, Aldrich Chemical Co., Milwaukee, USA), sodium triethylborohydride (1 M in THF, Aldrich Chemical Co.) and lithium triethylborohydride (Super-Hydride TM, 1 M in THF, Aldrich Chemical Co.). After the initial reaction between the species subsides, the mixture may be stirred at reflux to yield a homogenous reagent.

Alkali metal monochalcogenide reagents are created by reacting the alkali metal trialkylborohydride and the chalcogen in a molar ratio of about 2:1. The alkali metal dichalcogenide reagents are prepared by reacting the species in equimolar ratio.

The alkali metal chalcogen reagent so formed is then reacted with the appropriate aromatic halide to give the corresponding aromatic telluride or selenide. The reaction may be carried out in the same ether solvent system. Where heating beyond the boiling point of the ether solvent is necessary, the reaction may be performed in other compatible solvent systems. Suitable solvents for this purpose are polar aprotic solvents such as N,N-dimethylformamide and hexamethylphosphoramide. The reagent is simply transferred to a solution of the aromatic halide reactant in one of the polar aprotic solvents. Upon completion of the reaction, the product is then separated from the reaction mixture by extraction, chromatography, or other techniques well known to persons skilled in the art.

The alkali metal chalcogenide reagents formed from trialklyborohydrides are less reactive with aromatic and olefinic halides than alkali metal chalcogenide formed directly from chalcogen elements in polar aprotic solvents. Accordingly, the method gives products which are different in composition and yield from those prepared from previously described alkali metal chalcogenide reagents. For example, alkali metal selenide reagents prepared from alkali metal and selenium in polar aprotic solvent react with p-dibromobenzene to yield yellow poly-p-phenylene selenide (PPSe) having about 60 repeat units. In contrast, a Li$_2$Se reagent prepared from Li(C$_2$H$_5$)$_3$BH and Se in tetrahydrofuran gives a white solid oligomer which has fewer repeat units. The approximate oligomeric composition is Br—(C$_6$H$_4$—Se)$_{10}$Br.

Lower reactivity with olefinic halide compounds is also characteristic. For instance, heat is required to bring about reaction between the alkali metal chalcogenide reagent formed from trialkylborohydride and cis-dichloroethylene whereas reaction between the alkali metal chalcogenide reagent formed directly from the elements in an aprotic solvent and cis-dichloroethylene ensues at temperatures of −40° C. or lower.

In part, the different reactivity pattern may be due to the different composition of the reagent mixture. Also the difference may arise from the fact that the alkali metal chalcogenide reagent formed from trialkylborohydride in ether is a homogeneous solution whereas previously described alkali chalcogenide reagents in polar aprotic solvents are suspensions.

The invention is illustrated further by the following examples.

EXAMPLES

Example 1

Preparation of bis-(2-naphthyl)ditelluride by reaction of 2-chloronaphthalene with $Li_2Te_2$ from triethylborohydride Under argon atmosphere, $Li(C_2H_5)_3BH$ (10 mmole) in tetrahydrofuran (THF) was added via syringe to a suspension of tellurium (1.276 g, 0.01 gm-atom) in THF (10 ml). After the initial reaction subsided, the mixture was stirred at reflux for one hour to give a homogeneous purple reagent. This reagent was transferred via syringe to a solution of 2-chloronaphthalene (1.626 g, 10 mmole) in hexamethylphosphoramide (HMPA, 50 ml) under argon. The mixture was heated at a bath temperature of 140°–145° for 16 hours, followed by heating at 170°–175° for 24 hours. After cooling to room temperature, the mixture was suction filtered, the solid washed with dry HMPA (10 ml), and the filtrate slurried into brine (500 ml). The black precipitate was isolated by suction filtration and air-dried. The residue was extracted with methylene chloride (250 ml) which was evaporated. The residue was taken up in benzene (60 ml), chromatographed on silica gel packed in hexane, and eluted with hexane. The product bis-(2-naphthyl)ditelluride was recrystallized from hexane to give 0.446 g (17.5% yield), m.p. 121°–123°, homogeneous by thin layer chromatography.

Example 2

Preparation of Polyphenylene selenide by Reaction of p-Dibromobenzene with $Li_2Se$ from Triethylborohydride.

Under argon atmosphere 20 mmole $Li(C_2H_5)_3BH$ was added to selenium (0.790 gm, 0.01 gm-atom) in THF (10 ml) at 0°. After warming to room temperature and reflux for one hour, a milky white suspension was obtained. This reagent was added via syringe to N,N-dimethylformamide (DMF, 100 ml) containing p-dibromobenzene (2.359 g, 10 mmole) under argon. The mixture was heated at bath temperature of 140°–145° for 40 hours, and poly-p-phenyleneselenide (PPSe) was isolated in the usual manner to give 0.489 g (31.5% yield) of a white solid, m.p. 209°–214°, density 1.98 g/cm$^3$, which exhibited an infrared spectrum similar to previous samples of PPSe with the notable exception of reduced intensity near 290 cm$^{-1}$. The latter absorption had been attributed to diselenide linkages in the polymer. The X-ray diffraction of this sample of PPSe was similar to previous samples, and exhibited d-spacings at 4.97, 4.39, 4.07, 3.53, 3.24, 2.85, 2.74, 2.63, and 2.51 angstroms.

Analysis. Calculated for $-(C_6H_4Se)-_x$: C, 46.48; H, 2.60; Se, 50.92. Found: C, 43.54; H, 2.55; Se, 41.45; Br, 10.17. The observed composition corresponds to $Br-(C_6H_4Se-)_{10}Br$, MW ca. 1600.

Example 3

Reaction of cis-1,2-Dichloroethylene with $Li_2Se_2$ from Triethylborohydride

A $Li_2Se_2$ reagent was prepared under argon from $Li(C_3H_5)_3BH$ (20.8 mmole) added to selenium (1.596 g, 0.0202 gm-atom) in THF (12 ml) at room temperature and the mixure was heated to 65° over 2 hours. cis-1,2-Dichloroethylene (0.97 g, 10 mmole) was added at 65°, and the mixture was heated at 65° under static argon for 16 hours. The solvent was partially removed by distillation and the residue poured into brine (100 ml) to give a deep red solution. This was extracted with methylene chloride and the yellow solution dried over $Na_2SO_4$. Evaporation of the solution gave a yellow liquid (stench) found to contain at least six components by thin layer chromatography with $R_f$ values ranging from 0.04 to 0.91.

Example 4

Reaction of cis-1,2-Dichloroethylene with $Li_2Se_2$ from Triethylborohydride

The $Li_{Se2}$ reagent was prepared as in Example 3 on the same scale in 20 ml THF. To this mixture, DMF (20 ml) was added, and the mixture heated at 60° for 16 hours. cis-1,2-Dichloroethylene (0.97 g, 10 mmole) was added, and the mixture was heated at 60° for 6 hours. The mixture was poured into brine (300 ml), methylene chloride (100 ml) was added and the mixture was left in a refrigerator for ca. 70 hours. A red gummy material was separated from the mixture and washed with methylene chloride. This was dried at 120° and 10$^{-2}$ mm to give a dark rubbery gum, 0.786 g. This gum was found to contain deselenide linkages by its reduction with sodium borohydride in methanol. Further, it exhibited an infrared spectrum whose salient features included C-H stretching and diselenide absorption at 285 cm$^{-1}$.

Analysis. Calculated for $(C_2H_2Se_2)_n$: C, 13.06; H, 1.10; Se, 85.85. Found: C, 3.73; H, 0.63; Se, 93.27; Cl, 0.047.

Industrial Applicability

The method of the invention may be used to synthesize aromatic and olefinic molecular and polymeric tellurides, ditellurides, selenides and diselenides. Molecular and supramolecular aromatic tellurides, ditellurides and selenides have a variety of applications; they are useful as synthetic intermediates, photoconductive elements, lubricant additives, and bactericidal and anti-inflammatory agents. Further, many of these materials are precursors to organic conductive materials. For example, the heterocyclic compounds tetraseleno- and tetratellurotetracene are precursors to ion radical solids with low temperature metallic states. Tetratellurotetracene inerts with electron acceptors such as 7, 7, 8, 8-tetracyano-p-quinodimethane (TCNQ), iodine and ferric chloride to give conducting solids. R.P. Shibaeva et al., *Cryst. Struct. Comm.* 10,663(1981); Yagubskii et al., *Izv. Akad. Nauk SSR, Ser. Kim.*, 1432 (1981); Perez-Alberne, U.S. Pat. No. 3,754,986; Sandman, D. J. et al. *Mol. Cryst. Liq. Cryst.* 93:293 (1983). Another example of an electrically conductive organic chalcogenide prepared by the method of this invention is organic selenide polymer poly-p-phenylene selenide which becomes conductive when exposed to a strong oxidant such as arsenic pentafluoride. Sandman, D. J. et al. *J. Chem. Soc., Chem. Comm.*, pp. 1133–1134 (1982).

Equivalents

Those skilled in the art will recognize, or be able to ascertain, using no more than routine experimentation, numerous equivalents to the specific substances and procedures described herein. Such equivalents are considered to be within the scope of this invention and are covered by the following claims.

We claim:

1. A method of preparing aromatic organic telluride compounds comprising:

reacting elemental tellurium with an alkali metal trialkylborohydride in a solvent to produce a tellurium reagent and;

reacting said tellurium reagent with a carbocyclic aromatic halide having no strong electron withdrawing group other than a halogen on the halogenated ring or on a ring adjacent to the halogenated ring, in a reaction solution consisting of the tellurium reagent and the aromatic halide in a solvent, to form a carbocyclic aromatic organic telluride compound.

2. A method of claim 1 wherein the solvent is an ether.

3. A method of claim 1 wherein the alkali metal trialkylborohydride is sodium triethylborohydride, potassium tri-sec-butylborohydride or lithium triethylborohydride.

4. A method of preparing aromatic organic selenide compounds, comprising:

reacting elemental selenium with an alkali metal trialkylborohydride in a solvent to produce a selenium reagent; and reacting said selenium reagent with a carbocyclic aromatic halide having no strong electron withdrawing group other than a halogen on the halogenated ring or on a ring adjacent to the halogenated ring, in a reaction mixture consisting of the selenium reagent and the aromatic halide, to form a carbocyclic aromatic organic selenium compound.

5. A method of claim 4 wherein the solvent is an ether.

6. A method of claim 4 wherein the alkali metal trialkylborohydride is sodium triethylborohydride, potassium tri-sec-butylborohydride or lithium triethylborohydride.

7. A method of preparing bis-aryl ditellurides, comprising the steps of:

reacting in approximately equimolar ratio elemental tellurium and an alkali metal trialkylborohydride in a solvent to produce a tellurium reagent and;

reacting the tellurium reagent with a carbocyclic aryl monohalide having no strong electron withdrawing group other than the halogen on the halogenated ring or on a ring adjacent to the halogenated ring, to form a bis-aryl ditellurdie characterized by the formula Ar-Te-Te-Ar, wherein Ar signifies the carbocyclic aryl group of the aryl monohalide reactant, the reaction being performed in a reaction mixture consisting of the tellurium reagent and the aryl monohalide in a solvent.

8. A method of claim 7, wherein the solvent is an ether.

9. A method of claim 7, wherein the alkali metal trialkylborohydride is sodium triethylborohydide, potassium tri-sec-butylborohydride or lithium triethylborohydride.

10. A method of claim 7, wherein the aryl group is phenyl, naphthyl, authracenyl, tetracenyl, phenanthrenyl or biphenyl.

11. A method of preparing bis-aryl tellurides and aryl telluride polymers, comprising the steps of:

reacting in a molar ratio of about 1:2 elemental tellurium and an alkali metal trialkylborohydride in a solvent to produce a tellurium reagent and;

reacting the tellurium reagent with a carbocyclic aryl monohalide or a carbocyclic aryl dihalide, the aryl group having no strong electron withstanding group other than the halogen on the halogenated ring or on a ring adjacent to the halogenated ring, to form Ar-Te-Ar wherein Ar signifies the aryl group of the aryl monohalide reactant or to form a aryl telluride polymer generally characterized by the formula $(Ar-Te)_n$ wherein Ar signifies the carbocyclic aryl group of the aryl dihalide and n is an integer greater than 2, the reaction being performed in a reaction mixture consisting of the tellurium reagent and the aryl halide or dihalide in a solvent.

12. A method of claim 11, wherein the solvent is an ether.

13. A method of claim 11, wherein the alkali metal trialkylborohydride is sodium triethylborohydride, potassium tri-sec-butylborohydride or lithium triethylborohydride.

14. A method of claim 11, wherein the aryl group is phenyl, naphthyl, authracenyl, tetracenyl, phenanthrenyl or biphenyl.

15. A method of preparing bis-aryl diselenide, comprising the steps of:

reacting in approximately equimolar ratio elemental selenium and an alkali metal trialkylborohydride in a solvent to produce a selenium reagent; and reacting the selenium reagent with a carbocyclic aryl monohalide having no strong electron withdrawing group other than the halogen on the halogenated ring or on a ring adjacent to the halogenated ring, to form a bis-aryl diselenide characterized by the formula Ar-Se-Se-Ar, wherein Ar signifies the aryl group of the carbocyclic aryl monohalide reactant, the reaction being performed in a reaction mixture consisting of the selenium reagent and the aryl monohalide in a solvent.

16. A method of claim 15, wherein the solvent is an ether.

17. A method of claim 15, wherein the alkali metal trialkylborohydride is sodium triethylborohydride, potassium tri-sec-butylborohydride or lithium triethylborohydride.

18. A method of claim 15, wherein the aryl group is phenyl, naphthyl, authracenyl, tetracenyl, phenanthrenyl or biphenyl.

19. A method of preparing bis-aryl selenides and aryl selenide polymers, comprising the steps of:

reacting in a molar ratio of about 1:2 elemental selenium and an alkali metal trialkylborohydride in a solvent to produce a selenium reagent; and reacting the selenium reagent with a carbocyclic aryl monohalide or a carbocyclic aryl dihalide, the aryl group having no strong electron withstanding group other than the halogen on the halogenated ring or on a ring adjacent to the halogenated ring, to form Ar-Se-Ar wherein Ar signifies the carbocyclic aryl group of the aryl monohalide reactant or to form a aryl selenide polymer generally characterized by the formula $(Ar-Se)_n$ wherein Ar signifies the carbocyclic aryl group of the aryl dihalide and n is an integer greater than 2, the reaction being performed in a reaction mixture consisting essentially of the selenium reagent and the aryl halide or dihalide in a solvent.

20. A method of claim 19, wherein the solvent is an ether.

21. A method of claim 19, wherein the alkali metal trialkylborohydride is sodium triethylborohydride, potassium tri-sec-butylborohydride or lithium triethylborohydride.

22. A method of claim 19, wherein the aryl group is phenyl, naphthyl, anthracenyl, tetracenyl, phenanthrenyl or biphenyl.

* * * * *